United States Patent [19]

Wollemann et al.

[11] Patent Number: 4,474,987
[45] Date of Patent: Oct. 2, 1984

[54] PROCESS FOR PREPARING N,N-DISUBSTITUTED P-PHENYLENEDIAMINE DERIVATIVES

[75] Inventors: Bruno Wollemann, Muehltal; Hartmut Härtner, Weiterstadt; Hans Bardonner, Bad-Koenig, all of Fed. Rep. of Germany

[73] Assignee: Merck Patent Gesellschaft mit beschränkter Haftung, Darmstadt, Fed. Rep. of Germany

[21] Appl. No.: 365,131

[22] Filed: Apr. 5, 1982

Related U.S. Application Data

[63] Continuation of Ser. No. 218,249, Dec. 19, 1980, abandoned.

[30] Foreign Application Priority Data

Dec. 19, 1979 [DE] Fed. Rep. of Germany ....... 2951100

[51] Int. Cl.³ ............................................. C07C 85/11
[52] U.S. Cl. .................................. 564/420; 564/410; 564/421; 564/422; 564/423
[58] Field of Search ............... 564/410, 420, 421, 422, 564/423

[56] References Cited

U.S. PATENT DOCUMENTS

2,782,235 2/1957 Lantz et al. ......................... 564/410
2,811,555 10/1957 Larive et al. .................... 564/410 X

OTHER PUBLICATIONS

Bent et al., "J. Amer. Chem. Soc.", 73, pp. 3100–3125, 1951.

*Primary Examiner*—Paul F. Shaver
*Attorney, Agent, or Firm*—Millen & White

[57] ABSTRACT

A process for preparing an N,N-disubstituted p-phenylenediamine of the formula

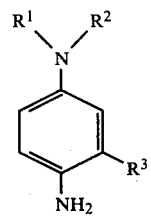

wherein $R^1$ is alkyl of 1–6 C atoms, $R^2$ is alkyl of 1–6 C atoms or alkyl of 1–6 C atoms which is substituted by OH, lower alkoxy, a sulfo group or an alkylsulfonamido group and $R^3$ is hydrogen or lower alkyl
or an acid addition salt thereof,
comprises adding an alkyl nitrite, as a nitrosation agent,
to an aqueous, acid suspension of the corresponding aniline derivative of the formula

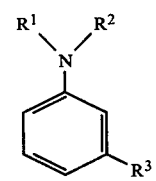

thereby forming the corresponding N,N-disubstituted p-nitroso-aniline, and subsequently hydrogenating the latter without isolation thereof from the reaction mixture.

7 Claims, No Drawings

4,474,987

PROCESS FOR PREPARING N,N-DISUBSTITUTED P-PHENYLENEDIAMINE DERIVATIVES

This is a continuation, of application Ser. No. 218,249 filed Dec. 19, 1980 now abandoned.

BACKGROUND OF THE INVENTION

The present invention relates to a new process for preparing N,N-disubstituted p-phenylenediamine derivatives of formula I

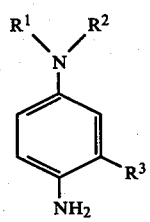

wherein $R^1$ is alkyl of 1 to 6 C atoms, $R^2$ is alkyl of 1 to 6 C atoms or alkyl of 1 to 6 C atoms which is substituted by OH, lower alkoxy, a sulfo group or an alkylsulfonamido group, and $R^3$ is hydrogen or lower alkyl, and acid addition salts thereof, by nitrosation of the corresponding aniline derivatives and subsequent hydrogenation of the N,N-disubstituted p-nitroso-aniline derivatives formed.

Such N,N-disubstituted p-phenylenediamine derivatives have been known for a long time (compare, for example, J.Amer.Chem.Soc. 73, 3,100, 1951). They have achieved great importance, in particular, as developer substances for color photography and also as intermediate products in the preparation of a very wide range of azo dyestuffs. Because the importance of these substances, which are at present already required in large amounts, is increasing further and the demand for them is rising, a number of processes, and in particular improved process conditions, are already known for the preparation of these compounds. However, in all the known processes for preparing N,N-disubstituted p-phenylenediamine derivatives, sodium nitrite is used for the nitrosation of the corresponding aniline derivatives. This nitrosation is carried out in aqueous or aqueous-alcoholic solution. Adding the nitrous acid required for the nitrosation in the form of its sodium salt requires, however, that the sodium added must be separated off again in the form of an inorganic salt after the nitrosation or, at the latest, after the subsequent hydrogenation to give the corresponding p-phenylenediamine derivatives. Furthermore, a number of undesired, troublesome by-products and, in particular secondary products are formed in this procedure. It is therefore necessary for the organic intermediate products and end products to be intermediately isolated and purified, even if, as proposed in a review (J.Amer.Chem.Soc. 73, 3,100, 1951), the reaction mixture containing the p-nitroso-aniline derivative is employed directly in the subsequent hydrogenation. Moreover, the intermediate presence of the unstable free p-phenylenediamine bases, which in some cases are allergenic, cannot be avoided in this procedure.

Although the problems occurring in the preparation of N,N-disubstituted p-phenylenediamine derivatives, that is to say the formation of undesired, troublesome by-products and secondary products, losses in yield, inadequate purity of the end products and the handling of unstable intermediate products, which in some cases are allergenic, have been recognized, a successful solution to these problems has not yet been proposed anywhere.

SUMMARY OF THE INVENTION

Accordingly, it is an object of this invention to improve the known processes so that the desired products are obtained in a higher purity and better yield, the formation of undesired by-products and secondary products is suppressed and intermediate isolation operations and purification steps can be avoided.

Upon further study of the specification and appended claims, further objects and advantages of this invention will become apparent to those skilled in the art.

These objects have been achieved by providing a process for preparing an N,N-disubstituted p-phenylenediamine derivative of formula I

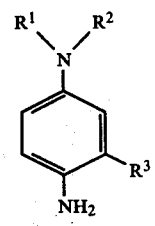

where $R^1$ is alkyl of 1 to 6 C atoms, $R^2$ is alkyl of 1 to 6 C atoms or alkyl of 1 to 6 C atoms which is substituted by OH, lower alkoxy, a sulfo group or an alkylsulfonamido group, and $R^3$ is hydrogen or lower alkyl, and acid addition salts thereof, by nitrosation of the corresponding aniline derivative and subsequent hydrogenation of the N,N-disubstituted p-nitroso-aniline derivative which is formed, wherein an alkyl nitrite is added, as the nitrosation agent, to an aqueous, acid suspension of the aniline derivative and the p-nitroso-aniline derivative formed is employed in the subsequent hydrogenation stage without being isolated.

DETAILED DISCUSSION

In fact, it has been found that, surprisingly, the yield of N,N-disubstituted p-phenylenediamine derivatives can be considerably increased by such a preparation method. Moreover, the quality of the end products can be decidedly improved, and a number of intermediate isolation operations and purification processes can be obviated by carrying out the nitrosation of the corresponding aniline derivatives in aqueous, acid suspension using an alkyl nitrite as the nitrosating agent and employing the p-nitroso-aniline derivative formed in the subsequent hydrogenation stage without isolation.

The advantages of the process of this invention include the very high yields of the desired end products since intermediate isolation operations and purification processes, which are associated with losses in yield, can be avoided. The main advantage of the procedure of this invention is, however, an unforeseeable improvement in the quality of the end products per se. Using this new process, they are obtained in an exceptionally pure form and in a better quality for their intended use.

The nitrosation with alkyl nitrites, particularly with amyl nitrite, is indeed known in principle. According to Berichte 8, pages 616 and 621 (1875), dimethylaniline and diethylaniline have been converted into the corresponding nitroso compound using amyl nitrite. However, this reaction, which has been known for more than 100 years (see also in Houben-Weyl, volume 10/I, page 1,040), has never been applied to the synthesis of color developers.

All the conventional nitrosation reactions carried out with alkyl nitrites have taken place in the presence of organic solvents, in particular alcohol, the alcohol being added as the solvent and not only being formed as a reaction component.

It is all the more surprising that it has now been found that the best results are achieved if, in contrast with the teachings of the state of the art, the reaction with the organic nitrite is carried out under the conditions usually used in the case of inorganic nitrites, that is to say in purely aqueous, acid solution. The organic solvent can thereby be eliminated along with the requirement of its subsequent removal.

This simple solution of the longstanding problem seems all the more remarkable since a conflicting proposal has just been made for the same problem. That is, in Japanese Laid-Open Specification 14731/77 (laid open on 3.2.1977), the addition of alcohol in the nitrosation with sodium nitrite is suggested for the preparation of purer color developer products in a better yield. It is highly probable that alkyl nitrite is also intermediately formed during this reaction. However, the inorganic salts must be separated off in this case also, since an alkali metal nitrite is employed. Furthermore, the nitroso compound obtained must be isolated and the free, unstable p-phenylenediamine base, which is a health hazard, is obtained in the subsequent hydrogenation. Moreover, excess acid is necessary to liberate the nitrous acid from the sodium nitrite and to separate off the sodium in the form of an inorganic salt.

This literature reference thus leads directly away from the teaching of this invention. The advantages which the addition of an alkyl nitrite prepared outside the reaction solution provides have not hitherto been discovered.

It was also known per se that the nitrosation could be carried out in the presence of acid. One particularly advantageous embodiment of the present process, however, requires that a quite definite amount of acid be added, i.e., approximately the amount (and type) of acid necessary for formation of the desired end product acid addition salt of the corresponding p-phenylenediamine derivative. The total amount of acid required is thereby reduced considerably in comparison with a nitrosation using sodium nitrite. Matching the acid exactly to requirements moreover enables optimization of the procedure employed to produce the end product. The formation of the solution by simple addition of the starting materials, in particular the corresponding acid, in the desired amount can be retained over all the subsequent stages and has an advantageous effect, especially on the subsequent hydrogenation. Further adjustment of the acid content before the start of the hydrogenation, previously as a rule necessary to determine that acid was still present, is no longer necessary. The desired acid addition salts of the N,N-disubstituted p-phenylenediamine derivatives are then precipitated directly from the reaction solution, generally by adding alcohol. In this manner, it is also possible to prevent the formation of the free p-phenylenediamine bases throughout the entire synthesis. Losses in yield and impairments in quality are thereby avoided, since, as is known, the bases are sensitive to oxidation, and intermediate purification operations can be eliminated. Working with the bases, which in some cases are allergenic, is also avoided.

The process of this invention thus opens up a surprisingly simple and successful route for the preparation of the p-phenylenediamine derivatives.

The N,N-disubstituted p-phenylenediamine derivatives of formula I and their acid addition salts, as well as the starting material N,N-disubstituted aniline derivatives and the corresponding N,N-disubstituted p-nitrosoaniline derivatives obtained as intermediate products are all known, for example from J.Amer.-Chem.Soc. 73, 3,100 (1951).

In a compound of the formula I, $R^1$ is alkyl of 1 to 6 C atoms, preferably of 2 to 4 C atoms, in particular ethyl. $R^2$ is alkyl of 1 to 6 C atoms or alkyl of 1 to 6 C atoms substituted by OH, lower alkoxy (e.g., of 1–4 C atoms), a sulfo group or a $C_{1-2}$-alkylsulfonamido group. Particularly preferred alkyl groups are those of 2 to 4 C atoms, and in particular those with 2 C atoms. If the alkyl group is substituted, terminal substitution is preferred. Lower alkoxy is preferably alkoxy of 1 to 4 C atoms, in particular methoxy. Alkylsulfonamido is, in particular, methyl- or ethyl-sulfonamido. $R^3$ is preferably hydrogen or methyl.

Preferred suitable acid addition salts are the corresponding monohydrochlorides, hemi-sulfates, sulfates and sequi-sulfates, and also oxalates and phosphates. The compounds can be in the form of the hydrated or anhydrous acid addition salts.

The known N,N-disubstituted aniline derivatives employed as starting materials can be prepared by known processes, for example by reaction of aniline or m-toluidine or of a monoalkyl aniline or monoalkyl-m-toluidine with substituted or unsubstituted alkyl halides or alkyl sulfates.

In principle, all alkyl nitrites can be used as the nitrosating agents. These should be metered in slowly during the reaction. The alkyl nitrites preferably used are alkyl nitrites of 1 to 6 C atoms, in particular, branched alkyl nitrites, such as iso-propyl nitrite, iso-butyl nitrite and iso-pentyl nitrite, but also methyl nitrite, ethyl nitrite, n-propyl nitrite, n-butyl nitrite, n-pentyl nitrite or n-hexyl nitrite. The particular alkyl nitrites employed are prepared outside the reaction mixture by known processes, for example by reacting an alkali metal nitrite with the desired alcohol in the presence of the equivalent amount of an acid, such as, for example, hydrochloric acid or sulfuric acid.

In a particularly advantageous embodiment of the process of this invention, the alkyl nitrite employed for the nitrosation is that which corresponds to the alcohol used for precipitating the acid addition salts of the N,N-disubstituted p-phenylenediamine derivatives from the reaction solution after hydrogenation. Such a procedure avoids entry of an additional constituent into the reaction system. Fractional distillation, which is otherwise necessary, can thus be avoided. If the precipitation of the acid addition salt of the p-phenylenediamine derivative is effected, for example, by adding isopropanol, isopropyl nitrite is preferably used for the nitrosation.

An aqueous, acid solution is used for carrying out the nitrosation of this invention. Acids which can be employed include all the inorganic acids. The nitrosation is preferably carried out in aqueous hydrochloric acid solution or aqueous sulfuric acid solution. In principle, only catalytic amounts of acid are necessary for carrying out the nitrosation. However, a particularly advantageous variant of the process of this invention is carried out in the presence of approximately the amount of acid necessary for the formation of the acid addition salt of the N,N-disubstituted p-phenylenediamine derivative concerned, which is formed in the subsequent hydrogenation stage.

The nitrosation is carried out at a temperature of about −20° to +100° C., preferably −5° to +5° C. The reaction time depends on the period over which the alkyl nitrite is introduced. As a rule it is 2 to 5 hours. When the reaction has ended, any excess of nitrite which is present can be removed in the customary manner, for example by adding urea or amidosulfonic acid.

In general, the amount of alkyl nitrite is 0.95–1.05 moles per mole of starting material aniline derivative, equimolar amounts are preferred. The aniline derivative is normally suspended in an aqueous acid medium in an amount of 10–40 wt.% based on the total weight of suspension.

The N,N-disubstituted p-nitroso-aniline derivative obtained by the nitrosation step of this invention is employed directly in the subsequent hydrogenation stage without being isolated from the reaction mixture. The hydrogenation of the resulting p-nitroso-aniline derivatives to produce the corresponding p-phenylenediamine derivatives is carried out by known processes and under known reaction conditions, such as are described, for example, in J.Amer.Chem.Soc. 73, 3,100 (1951). The nitroso compounds can be catalytically hydrogenated; examples of suitable catalysts include Raney nickel, Raney cobalt, platinum, platinum oxide, palladium or palladium-on-charcoal. However, it is also possible to carry out the hydrogenation with zinc dust in acid solution, preferably in hydrochloric acid solution. The hydrogenation is generally carried out in aqueous solution.

Since the free N,N-disubstituted p-phenylenediamine derivatives are generally unstable and sensitive to oxidation and in some cases are allergenic, they are preferably precipitated from the aqueous-acid reaction mixture in the form of their acid addition salts. This is effected—if appropriate, after prior concentration of the solution by distilling off water—by adding an organic solvent, preferably an alcohol, ether or ketone. A lower alcohol of 1 to 6 C atoms, in particular ethanol, isopropanol or iso-butanol, is preferably used.

The process of the invention thus represents a valuable new process by which N,N-disubstituted p-phenylenediamine derivatives, large amounts of which are required, especially as developer substances for color photography, can be prepared in a simple manner, in high yield and in an improved purity and quality for their intended use.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

360 g of N-ethyl-N-(2-hydroxyethyl)-m-toluidine and 1,250 g of water are initially introduced into a stirred flask. 196 g of concentrated sulfuric acid are added, while stirring and cooling. During this addition, the internal temperature should not rise above 50°. After cooling to 0°, 187 g of isopropyl nitrite is allowed to run in slowly at −2° to +2°. The excess of nitrite is then removed in the customary manner with amidosulfonic acid. The reaction mixture is brought to room temperature and degassed under reduced pressure. 60 g of pre-reduced Pd/C (5%) is added to this solution as the catalyst and the N-ethyl-N-(2-hydroxyethyl)-3-methyl-4-nitroso-aniline, which has not been isolated, is hydrogenated at 20° to 40° under a gauge pressure of 0.4 bar of hydrogen. When the reaction has ended, the reaction batch is let down, the catalyst is filtered off and the reaction mixture is concentrated.

$4$N-ethyl-$4$N-(2-hydroxyethyl)-2-methyl-p-phenylenediamine sulfate monohydrate is obtained from the oily residue as a marketable product by precipitation with ethanol. M.p. 154°–159°. Yield: 561 g (90% of theory).

The isopropyl nitrite employed as the starting material can be prepared as follows:

278 ml of isopropanol is added to 235 g of sodium nitrite in 800 ml of water, while stirring, and the reaction mixture is warmed to 50°. 286 ml of concentrated hydrochloric acid is then slowly added, while stirring. The isopropyl nitrite which distils off is collected in a cooled receiver.

EXAMPLE 2

370 g of N-ethyl-N-(2-methylsulfonamido-ethyl)-m-toluidine is added to 236 g of sulfuric acid in 1,200 ml of water, while stirring and cooling. The internal temperature should not exceed 80° during this addition. The reaction mixture is cooled to 0°, 129 g of isopropyl nitrite is slowly passed in and, when the addition has ended, the reaction mixture is subsequently stirred for a further few minutes. The reaction mixture is warmed to room temperature and the excess of nitrite is removed in the customary manner with amido-sulfonic acid. The reaction mixture is then used directly in the catalytic hydrogenation to give $4$N-ethyl-$4$N-(2-methylsulfonamidoethyl)-2-methyl-p-phenylenediamine, without isolating the N-ethyl-N-(2-methyl-sulfonamido-ethyl)-3-methyl-4-nitroso-aniline formed. $4$N-ethyl-$4$N-(2-methylsulfonamidoethyl)-2-methyl-p-phenylenediamine sesqui-sulfate monohydrate is isolated from the resulting reaction mixture by precipitation with isopropanol. M.p. 126°–130°.

EXAMPLE 3

81.5 g of N,N-diethyl-m-toluidine is initially introduced into a stirred flask with 46 ml of hydrochloric acid in 400 ml of water, the reaction mixture is cooled to 0° and gaseous methyl nitrite is passed in, while stirring and cooling. When the introduction of methyl nitrite has ended, the reaction mixture is brought to room temperature, the excess of nitrite is removed in the customary manner by adding urea and the residual gases are removed by applying reduced pressure. The entire reaction mixture is then passed to the catalytic hydrogenation to give $4$N,$4$N-diethyl-2-methyl-p-phenylenediamine without the N,N-diethyl-3-methyl-4-nitroso-aniline formed being isolated. When the hydrogenation has ended, $4$N,$4$N-diethyl-2-methyl-p-phenylenediamine hydrochloride is isolated by precipitation with ethanol. M.p. 268°–272°.

The methyl nitrite employed as the starting material can be produced by running 100 g of 50% sulfuric acid into a suspension of 55 g of sodium nitrite in 100 ml of methanol and 100 ml of water at 40° to 50°.

EXAMPLE 4

149 g of N,N-diethylaniline and 800 g of water are initially introduced into a stirred flask and 108 g of concentrated hydrochloric acid is added, while stirring and cooling. The internal temperature should not exceed 50°. After cooling to 0°, 29 g of isopropyl nitrite is slowly allowed to run in at −2° to +2°. The reaction mixture is then brought to room temperature and the excess of nitrite is removed in the customary manner with amidosulfonic acid. The resulting reaction mixture is then catalytically hydrogenated without the N,N-diethyl-4-nitroso-aniline formed being isolated. The end product N,N-diethyl-p-phenylenediamine hydrochloride is then precipitated by adding isopropanol. M.p. 232°–237°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an N,N-disubstituted p-phenylenediamine of the formula

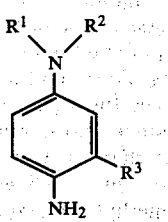

wherein $R^1$ is alkyl of 1–6 C atoms, $R^2$ is alkyl of 1–6 C atoms or alkyl of 1–6 atoms which is substituted by OH, lower alkoxy, a sulfo group or an alkylsulfonamido group and $R^3$ is hydrogen or lower alkyl or an acid addition salt thereof, comprising adding an alkyl nitrite, as a nitrosation agent, to an aqueous, acid suspension of the corresponding aniline derivative of the formula

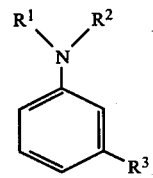

thereby forming the corresponding N,N-disubstituted p-nitroso-aniline, and subsequently hydrogenating the latter without isolation thereof from the reaction mixture.

2. A process of claim 1, wherein the nitrosation step is carried out in the presence of approximately the equivalent amount of acid necessary for formation of the acid addition salt of the N,N-disubstituted p-phenylenediamine, which is formed in the subsequent hydrogenation step.

3. A process of claim 1 or 2 wherein the N,N-disubstituted p-phenylenediamine is produced in the form of its acid addition salt and the salt is precipitated from the hydrogenation medium by addition of an alcohol, ether or ketone.

4. A process of claim 3 wherein the salt is precipitated by addition of an alkanol whose alkyl portion is the same as that of the alkyl nitrite employed in the nitrosation step.

5. A process of claim 1, wherein the nitrosation step is effected at room temperature of −20° to 100° C.

6. A process of claim 1, wherein the alkyl nitrite is branched.

7. A process of claim 1, wherein the alkyl nitrite is isopropyl nitrite, isobutyl nitrite or isopentyl nitrite.

* * * * *